United States Patent [19]

Hayakawa et al.

[11] Patent Number: 5,174,885
[45] Date of Patent: Dec. 29, 1992

[54] AIR FUEL RATIO SENSOR

[75] Inventors: Nobuhiro Hayakawa, Chita; Tessho Yamada, Nagoya, both of Japan

[73] Assignee: NGK Spark Plug Co. Ltd., Aichi, Japan

[21] Appl. No.: 596,438

[22] Filed: Oct. 12, 1990

[30] Foreign Application Priority Data

Oct. 13, 1989 [JP] Japan .................................. 1-266678

[51] Int. Cl.$^5$ ............................................. G01N 27/26
[52] U.S. Cl. .................................. 204/425; 204/424; 204/426; 204/427; 204/428; 204/429
[58] Field of Search ............... 204/425, 424, 426, 427, 204/428, 429

[56] References Cited

U.S. PATENT DOCUMENTS

| | | |
|---|---|---|
| 4,505,807 | 3/1985 | Yamada . |
| 4,568,443 | 2/1986 | Asayama et al. .................... 204/426 |
| 4,722,779 | 2/1988 | Yamada et al. ..................... 204/425 |
| 4,836,906 | 6/1989 | Yamada et al. ..................... 204/425 |

FOREIGN PATENT DOCUMENTS

| | | |
|---|---|---|
| 0142992 | 5/1985 | European Pat. Off. . |
| 0193379 | 9/1986 | European Pat. Off. . |
| 3606044 | 9/1986 | Fed. Rep. of Germany . |
| 3632456 | 4/1987 | Fed. Rep. of Germany . |
| 3703707 | 8/1987 | Fed. Rep. of Germany . |
| 3743435 | 7/1988 | Fed. Rep. of Germany . |
| 3910272 | 10/1989 | Fed. Rep. of Germany . |
| 61-47155 | 7/1986 | Japan . |
| 61-221644 | 10/1986 | Japan . |

Primary Examiner—John Niebling
Assistant Examiner—Bruce Bell
Attorney, Agent, or Firm—Sughrue, Mion, Zinn, Macpeak & Seas

[57] ABSTRACT

The invention provides an air/fuel ratio sensor, including an electrochemical sensor cell and an electrochemical pump cell, which shows both a quick response and a stable limiting current. This is realized by limiting the ratio of the area a of a region A to the area b of a region B on the inner electrode of the electrochemical sensor within a specified range, $0 < a/b \leq 0.1$. Here, the region A corresponds to a region C within a 0.5 mm distance from the end of the gas diffusion hole except on the 0.5 mm distance line on the inner electrode of the electrochemical pump cell, and the region B corresponds to a region D or the complement of the region C on the inner electrode of the electrochemical pump cell.

19 Claims, 9 Drawing Sheets

FIG. 8a NO. 1 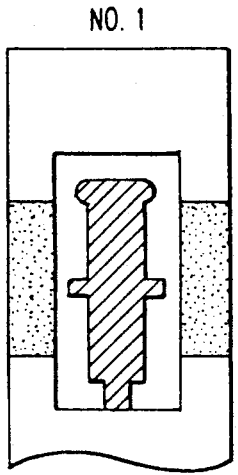
FIG. 8b NO. 2 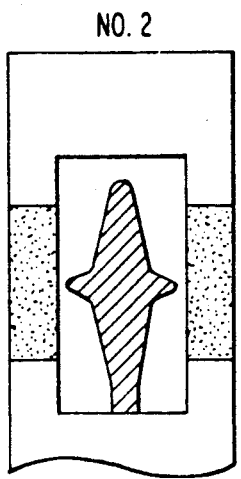
FIG. 8c NO. 3 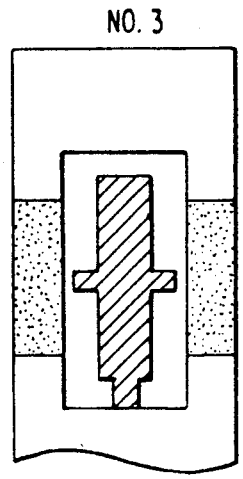
FIG. 8d NO. 4 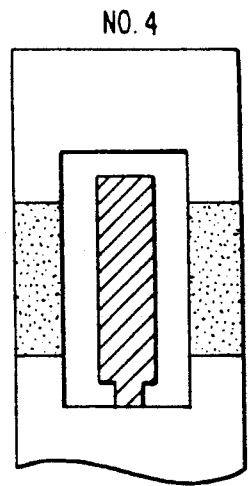
FIG. 8e NO. 5 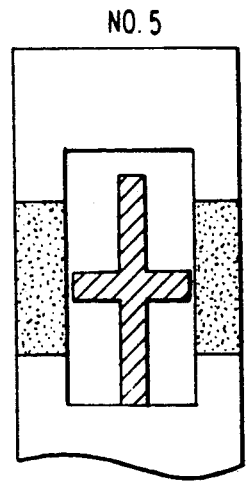
FIG. 8f NO. 6 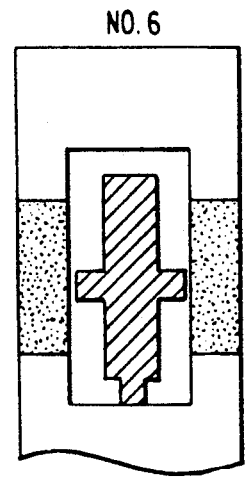
FIG. 8g NO. 7 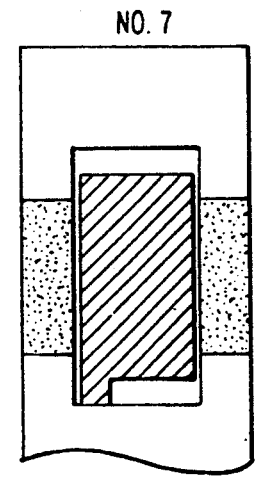

FIG. 9
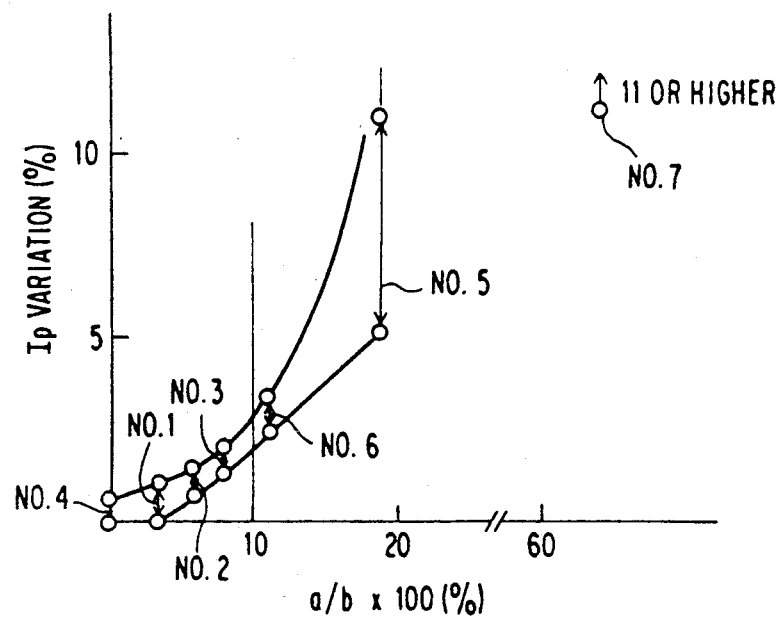
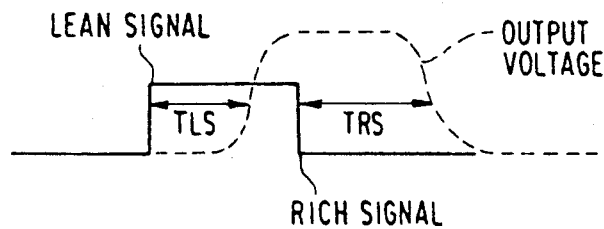
FIG. 10a
FIG. 10b
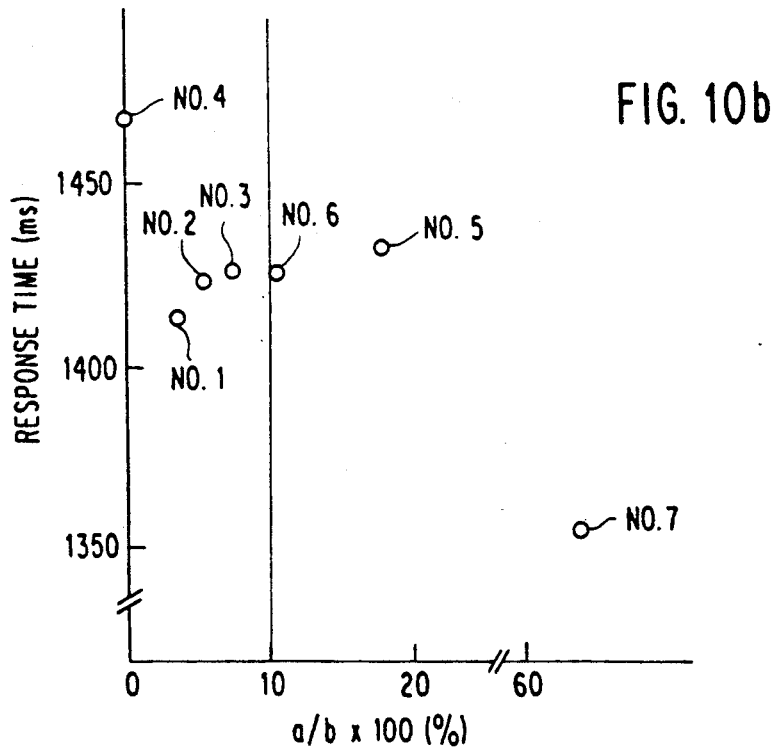

5,174,885

AIR FUEL RATIO SENSOR

BACKGROUND OF THE INVENTION

The present invention relates to an air/fuel ratio sensor for detecting the air/fuel ratio of an air and fuel mixture supplied to an engine and more particularly to an air/fuel ratio sensor including an oxide ion-conducting solid electrolyte.

An air/fuel ratio sensor, which measures the oxygen concentration in the exhaust discharge, is generally incorporated in an engine so as to improve the fuel consumption rate and emission. One type of well-known air/fuel ratio sensors includes an electrochemical pump cell (oxygen pump cell; Ip) and an electrochemical sensor cell (oxygen concentration cell; Vs) facing each other with a gas diffusion chamber in between, and a gas diffusion hole connecting the gas diffusion chamber to the outside.

Recently, various attempts have been made to improve the performance of the sensor in an atmosphere including substantially no oxides, e.g., $N_2$—$O_2$ dry air.

Japanese Published Unexamined patent application No. Sho-61-147155 has disclosed an improved sensor, which shows a stable limiting current in the Ip-Vs relation. The primary feature of the sensor is that the sizes of the electrode on the gas diffusion chamber side and of the diffusion chamber are respectively adjusted within a specified range.

Japanese Published Unexamined patent application No. Sho-61-221644 has proposed another improved sensor, which has two electrodes of identical size and exhibits a quick response.

The above sensors, however, still have some problems. Though the first sensor shows a stable limiting current even in dry air, it does not exhibit a sufficiently quick response. The second sensor shows a stable limiting current only in an atmosphere including neutral oxides such as $H_2O$ and $CO_2$, but not in dry air including substantially no oxides.

Wherefore, the object of the invention is thus to provide an air/fuel ratio sensor with a quick response; but, which shows a stable limiting current even in an atmosphere including substantially no oxides.

Other objects and benefits of the invention will become apparent from the detailed description which follows hereinafter when taken in conjunction with the drawing figures which accompany it.

SUMMARY OF THE INVENTION

The above and other related objectives are realized by an air/fuel ratio sensor which includes an electrochemical pump cell having porous electrodes on both sides of a solid electrolyte base, an electrochemical sensor cell having porous electrodes on both sides of a solid electrolyte base and facing the electrochemical pump cell via a gas diffusion chamber, and a gas diffusion hole connecting the gas diffusion chamber to the atmosphere; in which, the ratio of the area a of a region A to the area b of a region B on the inner electrode of the electrochemical sensor cell is within a specified range, which is expressed as follows: $0 < a/b \leq 0.1$; the region A corresponding to a region C within a 0.5 mm distance from the end of the gas diffusion hole except on the 0.5 mm distance line on the inner electrode of the electrochemical pump cell, and the region B corresponding to a region D or the complement of the region C on the inner electrode of the electrochemical pump cell.

The solid electrolyte bases of the electrochemical pump cell and sensor cell may be composed of one of the following solid solutions: yttrium (III) oxide ($Y_2O_3$)-zirconium (IV) oxide ($ZrO_2$), calcium oxide (CaO)-zirconium (IV) oxide ($ZrO_2$), cerium (IV) oxide ($CeO_2$), thorium (IV) oxide ($ThO_2$), hafnium (IV) oxide ($HfO_2$), perovskite ($CaTiO_3$), and oxides of trivalent metals.

The porous electrodes may be prepared in the following manner: Platinum or rhodium powder and one of the above solid solutions, e.g., yttrium oxide-zirconium oxide solid solution, are mixed with an organic solvent to form a paste-like mixture. A film of the mixture is printed onto either side of the solid electrolyte using a thick film printing method and the whole body is then sintered.

The outer porous electrode, located on the side far from the gas diffusion chamber, of the electrochemical pump cell directly comes into contact with the atmosphere. It is thus preferable to cover the surface of the porous electrode with a protection layer by a thick film printing method. The layer may be composed of aluminum oxide ($Al_2O_3$), spinel, zirconium (IV) oxide or mullite.

The gas diffusion chamber is formed by spacers between the electrochemical sensor cell and the pump cell. The preferable length of the gas diffusion chamber for a quick response is 20 through 100 $\mu$m.

The spacers may be composed of aluminum oxide, spinel, forsterite, steatite or zirconium oxide.

The gas diffusion hole of the gas diffusion chamber is a through-hole connecting the gas diffusion chamber to the atmosphere. The hole may be used empty or be filled with a porous material. The hole controls the flow rate of a gas into the gas diffusion chamber.

BRIEF DESCRIPTION OF THE DRAWINGS

The invention may be best understood by referring to the following detailed description of a preferred embodiment and the accompanying drawings, wherein like numerals denote like elements and in which:

FIGS. 8A through 8G are views showing the shapes of electrodes used in experiments for evaluating the performance of the air/fuel ratio sensor of FIG. 6;

FIG. 9 is a graph showing the Ip variation against $a/b \times 100$;

FIG. 10A is a graph showing the change-over of the air/fuel ratio between rich and lean;

FIG. 10B is a graph showing the response time against $a/b \times 100$; and

DETAILED DESCRIPTION OF PREFERRED EMBODIMENT

A preferred embodiment of the invention will now be explained in detail with particular reference to the drawings. Since there may be many modifications without departing from the scope and spirit of the invention, the embodiment below is not intended to limit the invention to that embodiment; but, is only intended to illustrate the invention more clearly.

Figure 1:
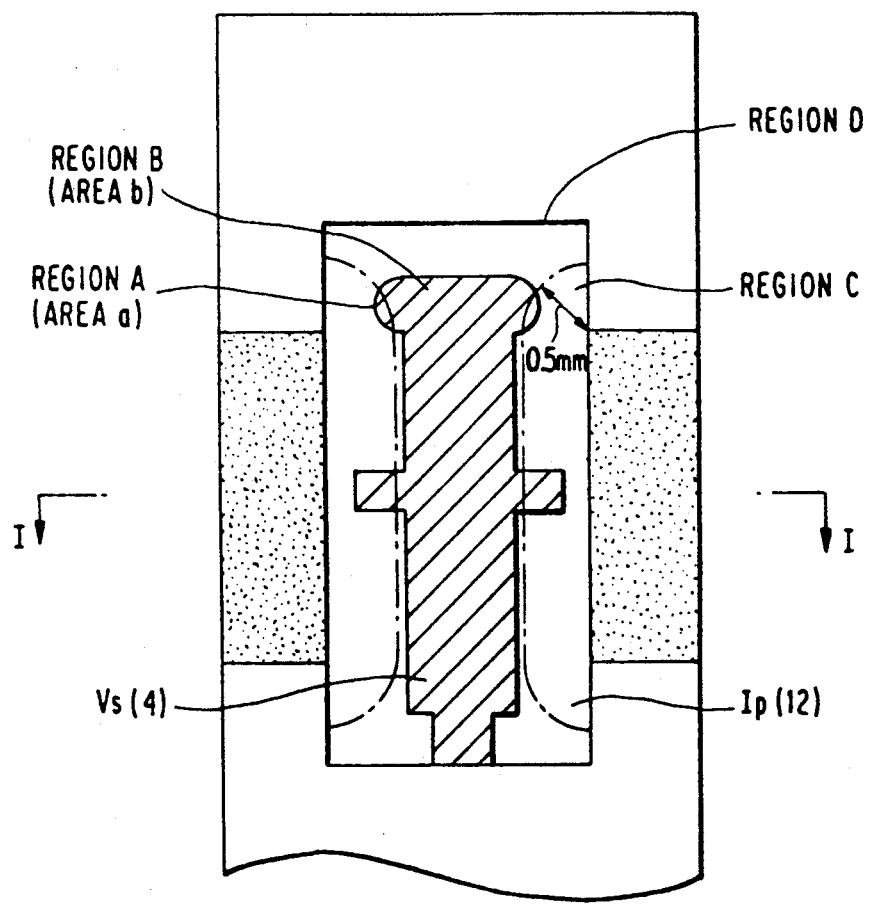
FIG. 1 is a simplified drawing showing the basic construction of an air/fuel ratio sensor according to the invention.

In an air/fuel ratio sensor according to the present invention as depicted in simplified form in FIG. 1, the area of a specified region on the inner electrode of the electrochemical sensor cell (hereinafter referred to as the Vs electrode) is controlled. The air/fuel ratio sensor thereby shows not only a quick response but also a stable limiting current even in an atmosphere including substantially no oxides. In FIG. 1, the inner electrode of the electrochemical pump cell (hereinafter referred to as the Ip electrode), which actually faces the Vs electrode, is shown overlapping with the Vs electrode for easy comparison of their sizes.

Within the range shown by the following expression, both a stable limiting current and a quick response are obtained:

$$0 < a/b \leq 0.1 \qquad (1)$$

where, a denotes the area of a region A on the Vs electrode; the region A corresponds to a region C within a 0.5 mm distance from the end of the gas diffusion hole except on the 0.5 mm distance line on the Ip electrode; b denotes the area of a region B on the Vs electrode; and the region B corresponds to a region D, i.e., the complement of the region C, on the Ip electrode.

The basis for determining the above range will now be explained in detail.

1. Limiting current

Figure 2:
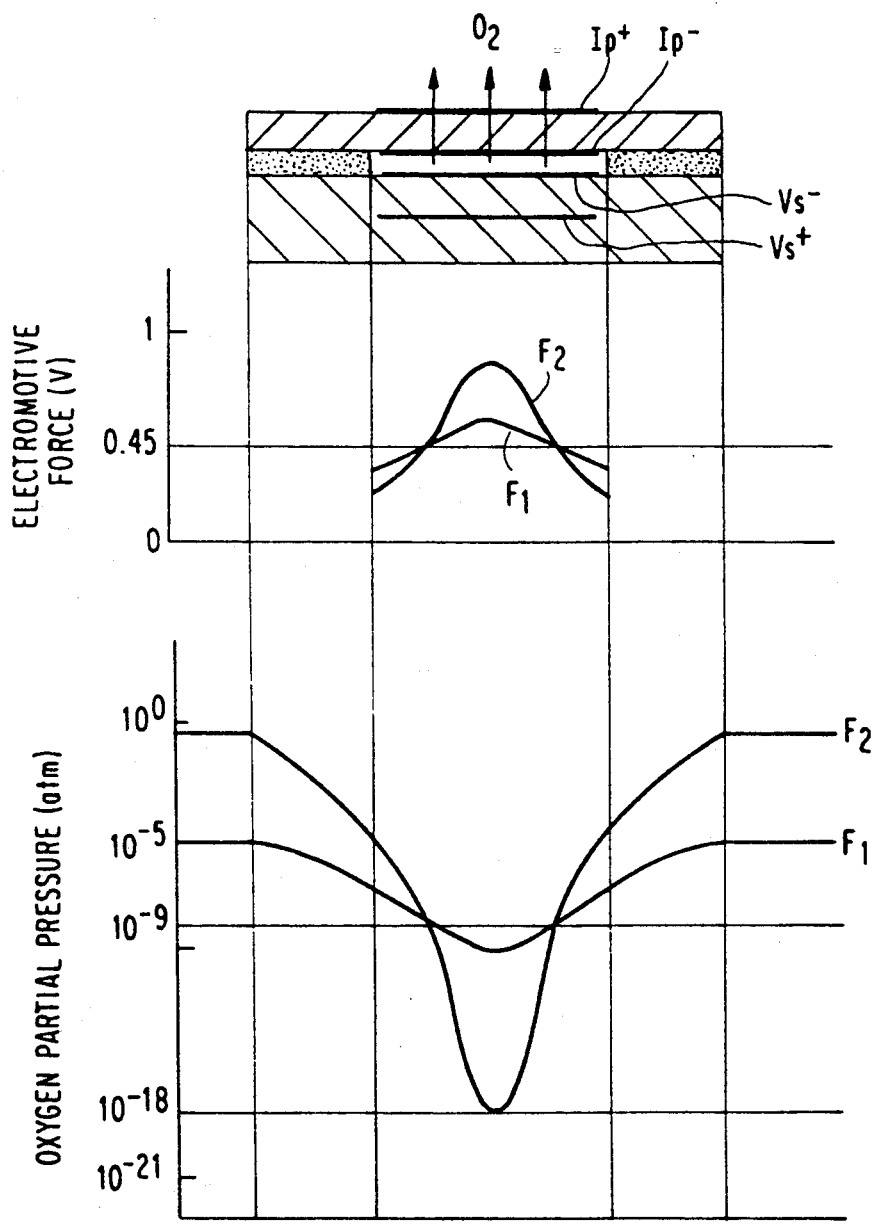
FIGS. 2 and 3 are drawings including performance graphs explaining the principle of the invention.
Figure 3:
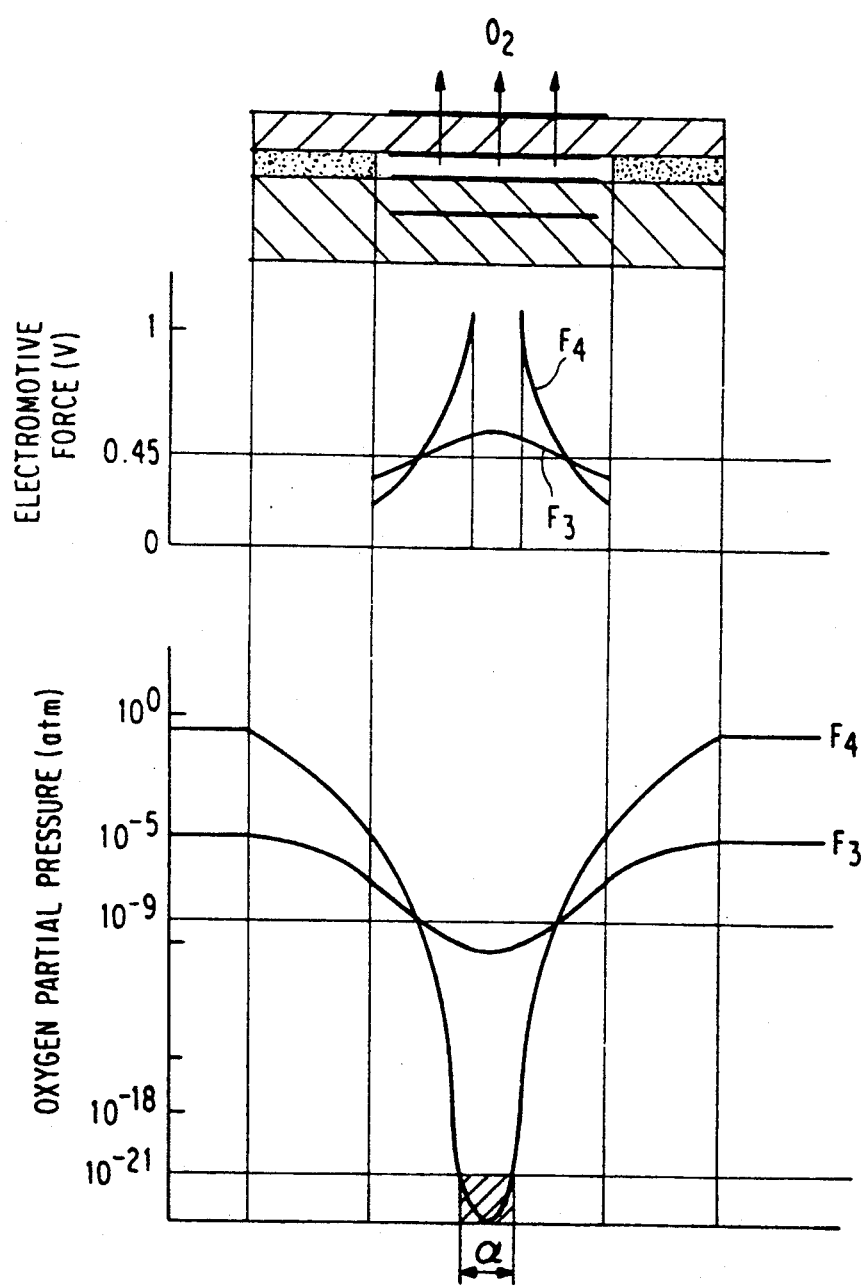

FIGS. 2 and 3 show the electromotive force and the oxygen partial pressure plotted against the position on the electrode of the air/fuel ratio sensor, which is shown as a cross sectional view taken on the line I—I of FIG. 1. Here, F2 shows the results measured in a general atmosphere including oxides such as $CO_2$ and $H_2O$, and F4 in a dry air such as $N_2$—$O_2$ including substantially no oxides.

As shown in FIG. 2, in the general atmosphere, the oxygen partial pressure curve F2 gives its lowest value, $10^{-18}$ atm, at the farthest position from the end of the gas diffusion hole, i.e., the center of the electrode. The lowest oxygen partial pressure is still sufficient to generate the electromotive force. The lower oxygen partial pressure produces the larger electromotive force as far as the partial pressure is greater than a certain value. The largest electromotive force is thus generated at the center of the electrode, as clearly seen on the electromotive force curve F2 in FIG. 2.

When oxides such as $H_2O$ or $CO_2$ exist in an atmosphere, they are dissociated by the Ip electrode to diffuse as $H_2$ or CO in the atmosphere, and the following reactions proceed on the Vs electrode or Ip electrode:

$$H_2 + \tfrac{1}{2}O_2 \rightleftharpoons H_2O \qquad (2)$$

$$CO + \tfrac{1}{2}O_2 \rightleftharpoons CO_2 \qquad (3)$$

The oxygen concentration on the Vs electrode is maintained relatively constant because of these reactions. The oxygen partial pressure thus shows a relatively high value even at the center of the electrode.

On the other hand, in dry air, the oxygen partial pressure curve F4 gives values lower than $10^{-21}$ atm at the farthest region from the end of the gas diffusion hole, i.e., a region A, as shown in FIG. 3. This region with the oxygen partial pressure lower than $10^{-21}$ becomes electron-conductive, and thus no electromotive force in generated therein.

Figure 4:
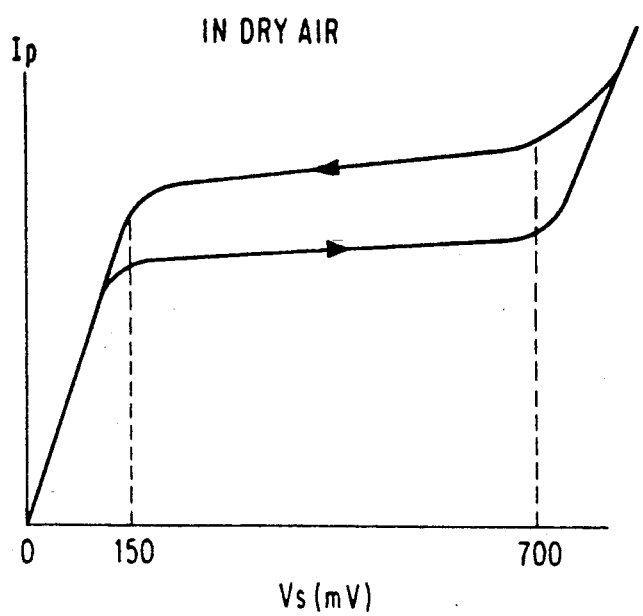
FIGS. 4 and 5 are graphs showing problems a conventional air/fuel ratio sensor may exhibit.
Figure 5:
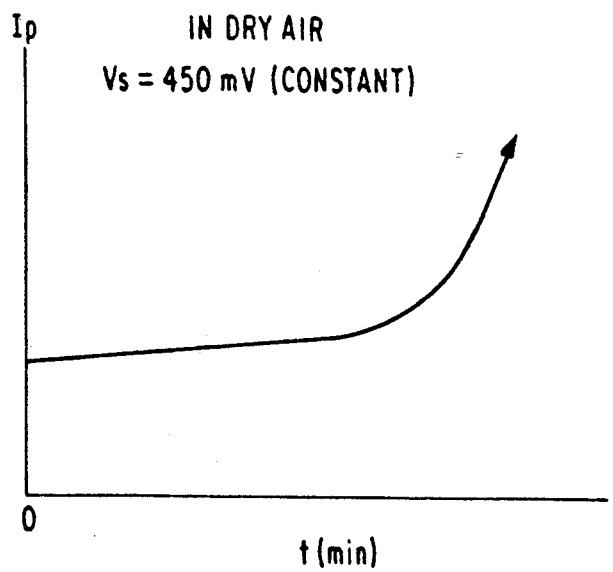

Since the dry air includes substantially no oxides, the above reactions (2) and (3) do not proceed and thus a large oxygen concentration gradient takes place on the Vs electrode. When the oxygen concentration is extremely low, the solid electrolyte becomes electron-conductive as well as ion-conductive. In such a case, hysteresis may occur in the Ip-Vs relation as shown in FIG. 4, or the Ip current may drastically change against the time as shown in FIG. 5.

In the air/fuel ratio sensor of this invention, the Vs electrode is located near the center of the sensor and the ratio a/b is limited within the range shown by the expression (1). The oxygen concentration is thus maintained relatively constant. A large electromotive force as well as a stable limiting current are thereby obtained.

2. Response

It is generally accepted in the art that the response of an air/fuel ratio sensor is enhanced when the same size of Vs and Ip electrodes are used in the sensor. With such a sensor, however, a stable limiting current is not obtained. To achieve the objectives of this invention, the area of the inner Vs electrode was reduced little by little to find the optimal condition for both a stable limiting current and a quick response. The optimal condition obtained is the range shown by the expression (1).

Figure 6:
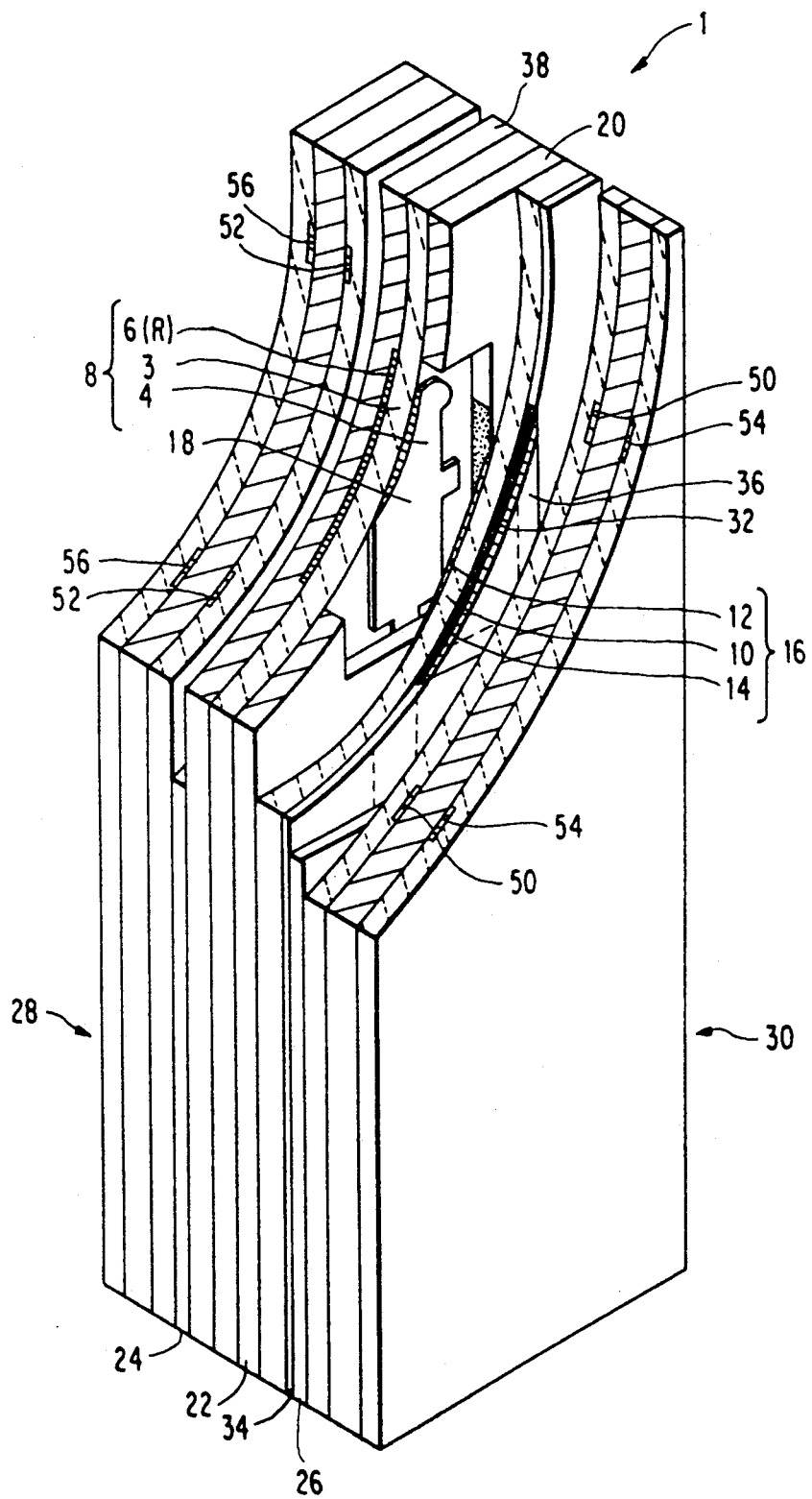
FIG. 6 is a perspective partially cutaway drawing illustrating an actual embodiment of an air/fuel ratio sensor according to the present invention.
Figure 7:
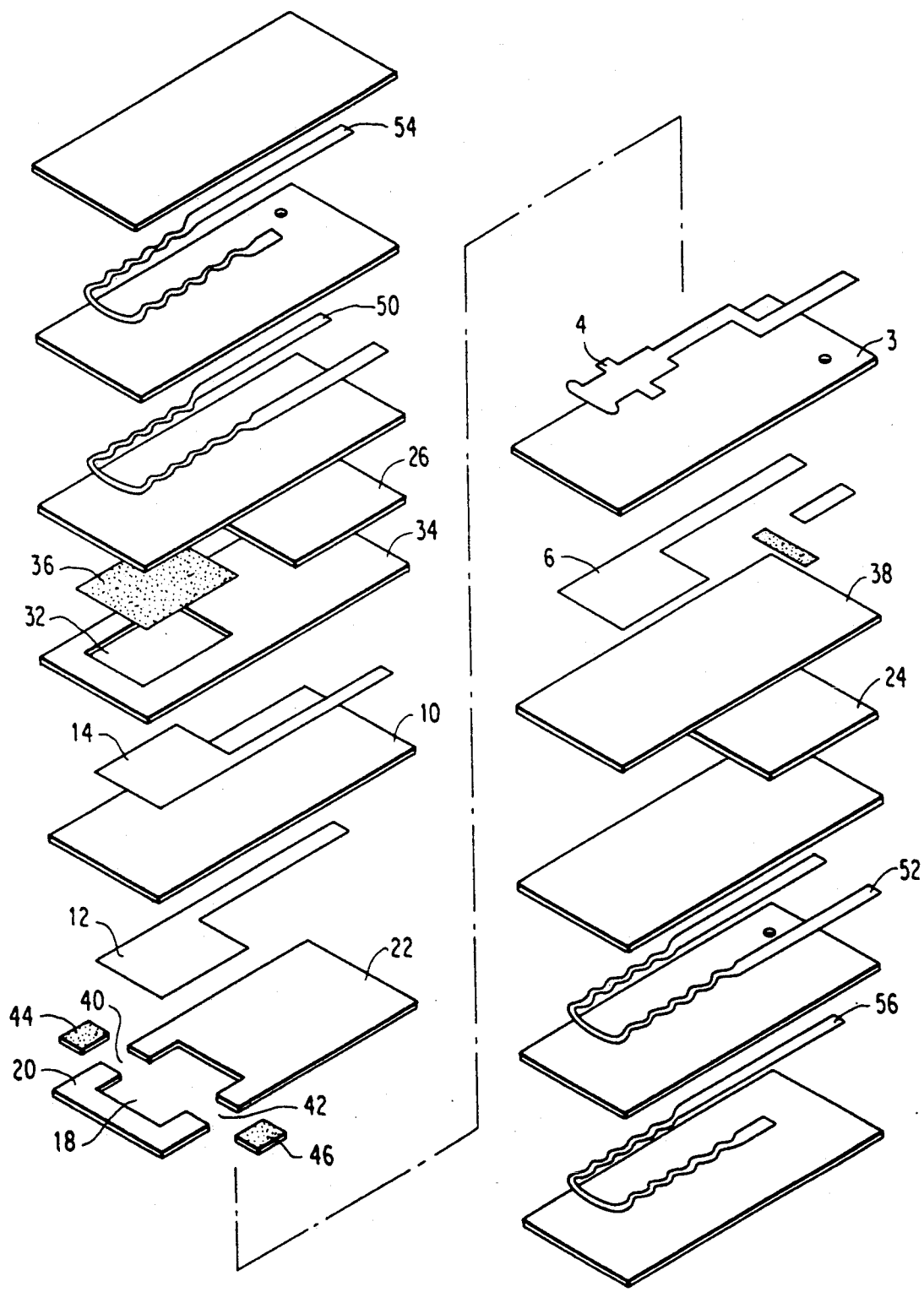
FIG. 7 is an exploded view illustrating the composition of the parts of FIG. 6.

Turning now to the construction of an actual sensor according to the above-described principles of the present invention, FIG. 6 is a perspective view with parts broken away, illustrating an air/fuel ratio sensor 1 embodying the invention and FIG. 7 is an exploded view illustrating the composition of the individual parts of the sensor 1.

As shown in FIGS. 6 and 7, the air/fuel ratio sensor 1 includes an electrochemical sensor cell (oxygen concentration cell) 8 having porous electrodes 4 and 6 on both sides of a solid electrolyte base 3, an electrochemical pump cell (oxygen pump cell) 16 having porous electrodes 12 and 14 on both sides of a solid electrolyte base 10, and upper and lower spacers 20 and 22 for forming a gas diffusion chamber in between the cells 8 and 16. Heaters 28 and 30 are mounted outside the electrochemical sensor cell 8 and the electrochemical pump cell 16 via spacers 24 and 26, respectively.

The rectangular porous electrodes 12 and 14 are attached on both sides of the solid electrolyte base 10 which is made of an yttrium oxide-zirconium oxide solid solution to form the electrochemical pump cell 16. The porous electrodes 12 and 14 are made of 16% by weight yttrium oxide-zirconium oxide solid solution and platinum.

The electrochemical pump cell 16 is covered with an insulator 34 made of aluminum oxide, which has a hole 32 for the porous electrode 14. The porous electrode 14 is covered with a porous layer 36, which is made of aluminum oxide and fits in the hole 32.

The electrochemical sensor cell 8 is constructed in substantially the same manner as the electrochemical pump cell 16. That is, the porous electrodes 4 and 6, made of 16% by weight yttrium oxide-zirconium oxide solid solution and platinum, are attached on both sides of the solid electrolyte base 3 which is composed of yttrium oxide-zirconium oxide solid solution.

As previously depicted in FIG. 1, the inner electrode 4 is a column in shape with a flange at the top and middle thereof and is placed to face the center of the porous electrode 12. The area and size of the electrode 4 are determined according to the range shown by the expression (1) as explained in detail above.

A shield layer 38 composed of a solid electrolyte is attached onto the outer electrode 6 of the electrochemical sensor cell 8. The shield layer 38 keeps the outer electrode 6 from being directly contacted by the atmosphere, thus allowing the electrode 6 to be used as an internal reference oxygen source R.

The U-shaped spacer 20 and the concave spacer 22 are made of aluminum oxide of 60 μm in thickness. The spacers 20 and 22 are provided in between the electrochemical pump cell 16 and the electrochemical sensor cell 8 to form the gas diffusion chamber 18. Gas diffusion holes 40 and 42 are provided on either side of the gas diffusion chamber 18 to connect the chamber 18 to the atmosphere, and are filled with porous fillers 44 and 46 made of aluminum oxide.

Exothermic patterns 50 and 52 are mounted on one side of the heaters 28 and 30 and migration preventing patterns 54 and 56 on the other side, respectively.

The manufacturing process of the air/fuel ratio sensor 1 will now be explained in further detail.

The solid electrolyte bases 3 and 10 of the electrochemical sensor cell 8 and of the electrochemical pump cell 16, respectively, are prepared as follows: Yttrium oxide-zirconium oxide powders are mixed with a PVB binder and an organic solvent to form a paste-like mixture. A thin film of the mixture is then produced by the doctor blade method.

The porous electrodes 4, 6 and 12, 14 of the electrochemical sensor cell 8 and of the electrochemical pump cell 16 are respectively prepared as follows: Zirconium oxide powder and yttrium oxide powder are mixed, sintered, pulverized and then dried to form an yttrium oxide-zirconium oxide base. 16% by weight yttrium oxide-zirconium oxide and platinum powder with the specific surface area of 10 m²/g or smaller (preferably 4 through 6 m²/g) are mixed with a cellulose or PVB binder and an organic solvent, e.g., butyl carbitol, to form a paste-like mixture. The mixture is then printed onto the either side of the solid electrolyte base 3 or 10 by a screen printing process.

The solid electrolyte bases 3, 10 with the porous electrodes 4 and 6, 12 and 14, the insulator 34, the shield layer 38 and other parts are pressure connected with one another and are sintered at 1,500° C. for one hour. The air/fuel ratio sensor 1 including the electrochemical sensor cell 8 and the electrochemical pump cell 16 is then complete.

Actual experiments for evaluating the performance of an air/fuel ratio sensor 1 according to the above-described embodiment will now be described.

Results of Experiments:

Vs electrodes (electrodes of the electrochemical sensor cell) of different shapes were prepared as shown in FIGS. 8A through 8G and were individually incorporated into the air/fuel ratio sensor 1. The samples labelled No. 1 through No. 3 are examples of the invention and No. 4 through No. 7 are references. Table 1 shows the depth x of the gas diffusion holes 40 and 42 and the ratio a/b in the examples and references.

TABLE 1

|  | No. | x [mm] | a/b |
|---|---|---|---|
| Examples | 1 | 0.8 | 0.033 |
|  | 2 | 0.8 | 0.06 |
|  | 3 | 0.8 | 0.08 |
| References | 4 | 0.8 | 0 |
|  | 5 | 0.8 | 0.18 |
|  | 6 | 0.8 | 0.11 |
|  | 7 | 0.8 | 0.64 |

The limiting current was measured as to the above examples and references.

The air/fuel ratio sensors 1 of the examples and references were located, respectively, in a $N_2$—$O_2$ dry air at 450° C. The voltage of the Vs electrode was controlled at a constant value 450 mV and the variation of the pump current Ip was measured. The variation of Ip is expressed as:

$$(Ip - Ip_0)/Ip_0 \times 100 \, [\%].$$

where, Ip denotes a pump current after one hour; and $Ip_0$ denotes the initial pump current.

FIG. 9 shows the results of the measurement. The Ip variation is plotted against a/b×100 [%]. The difference of the two curves shows the variation of the Ip current. In the air/fuel ratio sensors 1 of examples No. 1 through No. 3 and reference No. 4 with a a/b value of 10% or smaller, the variation of the Ip current was small and limiting currents obtained were stable. On the other hand, in the sensors 1 of references No. 5 through No. 7, the variation of the Ip current was large and the limiting currents obtained were unstable.

Response was also evaluated as to the examples and references. To do this, the air/fuel ratio sensors 1 of the examples and references were located in an exhaust gas discharged from a propane burner. The air/fuel ratio was changed between rich (λ=1.2) and lean (λ=0.8) states as shown in FIG. 10A and the response of the sensor 1 was evaluated. The response time $T_{LS}$ from lean to rich or $T_{RS}$ from rich to lean is a time period between the output of a rich or lean signal and a time point when the output voltage reaches 50% of the full value. The results are shown in FIG. 10B.

Examples No. 1 through No. 3 and references No. 5 through No. 7 showed quick response; but, reference No. 4 had a slower response.

As clearly shown in the results of the above experiments, each of the examples No. 1 through No. 3 showed both a stable limiting current and a quick response. On the other hand, No. 4 through No. 7 showed either a stable limiting current or a quick response, but not both.

Figure 11:
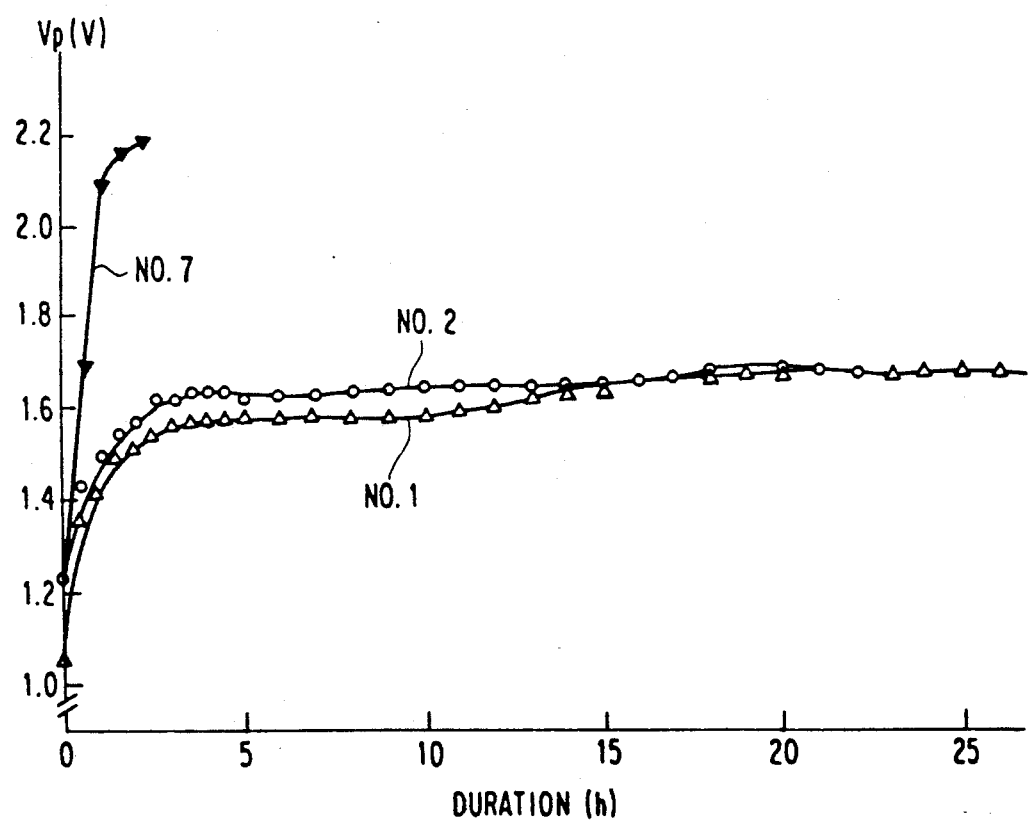
FIG. 11 is a graph showing the Vp voltage against the duration.

The anti-blackening characteristics were evaluated by measuring the pump voltage Vp in the air/fuel ratio sensors 1 of examples No. 1 and No. 2 and reference No. 7. Blacking is a phenomenon wherein the solid electrolyte deteriorates and becomes black due to the reduced oxygen concentration thereof. FIG. 11 shows the results of this experiment. In examples No. 1 and No. 2, the Vp voltage became flat approximately at 1.7 and did not rise any further; thus, blackening did not occur. On the other hand, in reference No. 7, the Vp voltage rose over 2V and blackening occurred. The air/fuel ratio sensors 1 of the examples also showed favorable anti-blackening characteristics.

As described above, the air/fuel ratio sensor of this invention shows both a stable limiting current and a quick response. This is realized by limiting the ratio of the area a of a region A to the area b of a region B on the inner electrode of an electrochemical sensor within a specified range, $0 < a/b \leq 0.1$. Here, the region A corresponds to a region C within a 0.5 mm distance from the end of the gas diffusion hole except on the 0.5 mm distance line on the inner electrode of an electrochemical pump cell, and the region B corresponds to a region D or the complement of the region C on the inner electrode of the electrochemical pump cell.

Wherefore, having thus described the present invention, What is claimed is:

1. An air/fuel ratio sensor comprising:
   (a) an electrochemical pump cell having porous inner and outer electrodes on respective sides of a solid electrolyte base;
   (b) an electrochemical sensor cell having porous inner and outer electrodes on respective sides of a solid electrolyte base, said inner electrode of said electrochemical sensor cell facing said inner electrode of said electrochemical pump cell on opposite sides of a gas diffusion chamber; and,
   (c) a gas diffusion conduit connecting said gas diffusion chamber to an atmosphere;
   (d) a Vs electrode, wherein the Vs electrode is the inner electrode of the electrochemical sensor cell;
   (e) an area "a" of the Vs electrode has a ratio with respect to an area "b" on said Vs electrode of said electrochemical sensor cell within the range, $0 < a/b < 0.1$;
   (f) wherein "a" is the total area of the Vs electrode which extends a distance of within less then 0.5 mm from an end of the gas diffusion chamber;
   (g) said area "b" is the total area of the Vs electrode minus the area "a".

2. The air/fuel ratio sensor of claim 1 wherein:
   a) said gas diffusion chamber is elongated having a length longer than a width thereof;
   b) said conduit communicates with said gas diffusion chamber at a center portion thereof; and,
   c) said inner electrode of said electrochemical sensor is elongated having a length longer than a width thereof, said inner electrode of said electrochemical sensor being positioned within said gas diffusion chamber with length axes thereof in alignment.

3. The air/fuel ratio sensor of claim 1 wherein:
   a) said gas diffusion chamber is rectangular in shape; and,
   b) said inner electrode of said electrochemical sensor has first protrusions on both sides of said length thereof at approximate mid-points thereof.

4. The air/fuel ratio sensor of claim 3 wherein:
   said inner electrode of said electrochemical sensor has second protrusions on both sides of said length thereof at an end adjacent said region D.

5. The air/fuel ratio sensor of claim 3 wherein:
   said inner electrode of said electrochemical sensor is generally rectangular in shape.

6. The air/fuel ratio sensor of claim 1 wherein:
   said gas diffusion chamber is formed by spacers disposed between said electrochemical sensor cell and said pump cell.

7. The air/fuel ratio sensor of claim 6 wherein:
   said spacers are composed of material selected from the group consisting of aluminum oxide, spinel, forsterite, steatite, and zirconium oxide.

8. The air/fuel ratio sensor of claim 1 wherein:
   for quick response said gas diffusion chamber is of a length between 20 and 100 $\mu$m.

9. The air/fuel ratio sensor of claim 1 wherein:
   said solid electrolyte base of said electrochemical pump cell and said solid electrolyte base of said sensor cell are composed of a solid solutions selected from the group consisting of yttrium (III) oxide ($Y_2O_3$)-zirconium (IV) oxide ($ZrO_2$), calcium oxide (CaO)-zirconium (IV) oxide ($ZrO_2$), cerium (IV) oxide ($CeO_2$), thorium (IV) oxide ($ThO_2$), hafnium (IV) oxide ($HfO_2$), perovskite ($CaTiO_3$), and oxides of trivalent metals.

10. The air/fuel ratio sensor of claim 1 and additionally comprising:
    a protective layer covering each of said porous outer electrodes.

11. The air/fuel ratio sensor of claim 10 wherein:
    said protective layer comprises a material selected from the group consisting of aluminum oxide ($Al_2O_3$), spinel, zirconium (IV) oxide, and mullite.

12. An air/fuel ratio sensor comprising:
    (a) an electrochemical pump cell having porous inner and outer electrodes on respective sides of a solid electrolyte base;
    (b) an electrochemical sensor cell having porous inner and outer electrodes on respective sides of a solid electrolyte base, said inner electrode of said electrochemical sensor cell facing said inner electrode of said electrochemical pump cell on opposite sides of a gas diffusion chamber; and,
    (c) a gas diffusion conduit connecting said gas diffusion chamber to an atmosphere; wherein,
    (d) said gas diffusion chamber is elongated having a length longer than a width thereof;
    (e) said conduit communicates with said gas diffusion chamber at a center portion thereof; and,
    (f) said inner electrode of said electrochemical sensor is elongated having a length longer than a width thereof, said inner electrode of said electrochemical sensor being positioned within said gas diffusion chamber with length axes thereof in alignment
    (g) a Vs electrode, wherein the Vs electrode is the inner electrode of the electrochemical sensor cell, and further wherein said air/fuel ratio sensor has the characteristics of:
    (h) an area "a" of the Vs electrode has a ratio with respect to an area "b" on said Vs electrode of said electrochemical sensor cell within the range, $0 < a/b < 0.1$;
    (i) wherein "a" is the total area of the Vs electrode which extends a distance of within less than 0.5 mm from the end of the gas diffusion chamber;;
    (j) said area "b" is the total area of the Vs electrode minus the area "a".

13. The air/fuel ratio sensor of claim 12 wherein:
    a) said gas diffusion chamber is rectangular in shape; and,
    b) said inner electrode of said electrochemical sensor has first protrusions on both sides of said length thereof at approximate mid-points thereof.

14. The air/fuel ratio sensor of claim 13 wherein:
    said inner electrode of said electrochemical sensor has second protrusions on both sides of said length thereof at an end adjacent said region D.

15. The air/fuel ratio sensor of claim 12 wherein:

said gas diffusion chamber is formed by spacers disposed between said electrochemical sensor cell and said pump cell.

16. The air/fuel ratio sensor of claim 15 wherein:
said spacers are composed of material selected from the group consisting of aluminum oxide, spinel, forsterite, steatite, and zirconium oxide.

17. The air/fuel ratio sensor of claim 12 wherein:
for quick response said gas diffusion chamber is of a length between 20 and 100 μm.

18. The air/fuel ratio sensor of claim 12 wherein:
said solid electrolyte base of said electrochemical pump cell and said solid electrolyte base of said sensor cell are composed of a solid solutions selected from the group consisting of yttrium (III) oxide ($Y_2O_3$)-zirconium (IV) oxide ($ZrO_2$), calcium oxide (CaO)-zirconium (IV) oxide ($ZrO_2$), cerium (IV) oxide ($CeO_2$), thorium (IV) oxide ($ThO_2$), hafnium (IV) oxide ($HfO_2$), perovskite ($CaTiO_3$), and oxides of trivalent metals.

19. The air/fuel ratio sensor of claim 12 and additionally comprising:
a protective layer covering each of said porous outer electrodes wherein said protective layer comprises a material selected from the group consisting of aluminum oxide ($Al_2O_3$), spinel, zirconium (IV) oxide, and mullite.

* * * * *